(12) United States Patent
Koyanagi et al.

(10) Patent No.: US 8,729,106 B2
(45) Date of Patent: May 20, 2014

(54) PESTICIDAL COMPOSITIONS

(75) Inventors: Toru Koyanagi, Kusatsu (JP); Masayuki Morita, Kusatsu (JP); Tetsuo Yoneda, Kusatsu (JP); Tsuyoshi Ueda, Kusatsu (JP); Kazuhisa Kiriyama, Kusatsu (JP); Taku Hamamoto, Kusatsu (JP)

(73) Assignee: Ishihara Sangyo Kaisha, Ltd., Osaka-shi (JP)

( * ) Notice: Subject to any disclaimer, the term of this patent is extended or adjusted under 35 U.S.C. 154(b) by 416 days.

(21) Appl. No.: 12/516,649

(22) PCT Filed: Dec. 12, 2007

(86) PCT No.: PCT/JP2007/074372
§ 371 (c)(1),
(2), (4) Date: May 28, 2009

(87) PCT Pub. No.: WO2008/072783
PCT Pub. Date: Jun. 19, 2008

(65) Prior Publication Data
US 2010/0028304 A1 Feb. 4, 2010

(30) Foreign Application Priority Data
Dec. 14, 2006 (JP) .................. 2006-336585
Apr. 12, 2007 (JP) .................. 2007-105029

(51) Int. Cl.
*A01N 43/40* (2006.01)
*A01N 25/32* (2006.01)

(52) U.S. Cl.
USPC ............. 514/341; 424/405; 514/355

(58) Field of Classification Search
CPC ............ A01N 25/006; A01N 25/40
USPC .................... 514/341, 355; 424/405
See application file for complete search history.

(56) References Cited

U.S. PATENT DOCUMENTS

| | | | |
|---|---|---|---|
| 7,612,100 B2 * | 11/2009 | Koyanagi et al. | 514/341 |
| 7,994,201 B2 * | 8/2011 | Koyanagi et al. | 514/341 |
| 2007/0129407 A1 * | 6/2007 | Koyanagi et al. | 514/341 |
| 2007/0142327 A1 | 6/2007 | Funke et al. | |
| 2007/0232598 A1 | 10/2007 | Funke et al. | |
| 2007/0270416 A1 | 11/2007 | Funke et al. | |
| 2008/0027114 A1 | 1/2008 | Funke et al. | |
| 2008/0070863 A1 | 3/2008 | Funke et al. | |
| 2010/0028304 A1 * | 2/2010 | Koyanagi et al. | 424/93.5 |
| 2010/0063293 A1 * | 3/2010 | Koyanagi et al. | 546/275.4 |

FOREIGN PATENT DOCUMENTS

| | | |
|---|---|---|
| EP | 1 717 237 | 11/2006 |
| WO | 2005 048711 | 6/2005 |
| WO | 2005 048712 | 6/2005 |
| WO | 2005 048713 | 6/2005 |
| WO | 2005 053405 | 6/2005 |
| WO | 2005 053406 | 6/2005 |
| WO | 2005 077934 | 8/2005 |
| WO | 2005077934 * | 8/2005 |
| WO | 2006 055922 | 5/2006 |
| WO | 2006118267 * | 11/2006 |
| WO | WO 2007/112893 A2 | 10/2007 |

OTHER PUBLICATIONS

U.S. Appl. No. 13/003,895, filed Jan. 13, 2011, Hamamoto.
U.S. Appl. No. 12/867,854, filed Aug. 16, 2010, Morita, et al.
U.S. Appl. No. 12/919,428, filed Aug. 25, 2010, Morita, et al.
Office Action issued May 7, 2013, in Japanese Patent Application No. 2007-314527 with English translation.
U.S. Appl. No. 12/519,177, filed Jun. 15, 2009, Koyanagi, et al.

* cited by examiner

*Primary Examiner* — Neil Levy
(74) *Attorney, Agent, or Firm* — Oblon, Spivak, McClelland, Maier & Neustadt, L.L.P.

(57) ABSTRACT

A pesticidal composition comprising synergistically effective amounts of at least one anthranilamide compound represented by the formula (I) or its salt and other pesticide: wherein each of $R_{1a}$ and $R_{1b}$ which are independent of each other, is halogen; each of $R_2$ and $R_3$ is halogen, alkyl, haloalkyl, alkoxy, haloalkoxy or cyano; A is alkyl substituted by Y; Y is $C_{3-4}$ cycloalkyl which may be substituted by at least one substituent selected from the group consisting of halogen, alkyl and haloalkyl; n is 0 or 1; and q is an integer of from 0 to 4; provided that $R_{1a}$ and $R_{1b}$ are not simultaneously chlorine nor bromine.

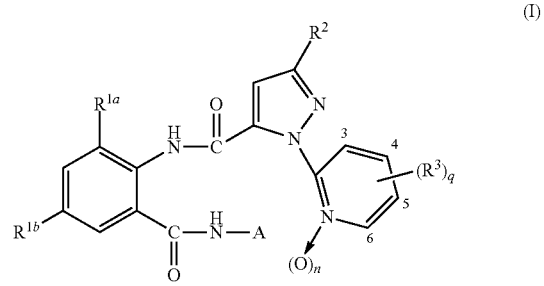

1 Claim, No Drawings

PESTICIDAL COMPOSITIONS

CROSS-REFERENCE TO RELATED APPLICATIONS

This application is a National Stage of PCT/JP07/074372 filed Dec. 12, 2007 and claims the benefit of JP 2006336585 filed Dec. 14, 2006 and JP 2007105029 filed Apr. 12, 2007.

TECHNICAL FIELD

The present invention relates to pesticidal compositions comprising anthranilamide compounds of the formula (I) described hereinafter or their salts and other pesticides.

BACKGROUND ART

Heretofore, an organophosphorus compound, a carbamate compound, a pyrethroid compound or the like has been used as an effective ingredient for an insecticide, but as this result, some insects have had a resistance to these insecticides in recent years. Therefore, it is demanded to provide an insecticide effective for these insects having a resistance.

An anthranilamide compound of the formula (I) described hereinafter or its salt is disclosed in Patent Document 1. Further, Patent Document 2 discloses in test A and test C at pages 83 to 85 a controlling effect of a combination of a specific anthranilamide compound with imidacloprid or thiamethoxam against diamondback moth or aphid.

Patent Document 1: WO2005/077934
Patent Document 2: WO2006/055922

DISCLOSURE OF THE INVENTION

Problems that the Invention is to Solve

Conventional pesticides have respectively characteristic spectrums and effects, but have some problems that the effects are sometimes unsatisfactory to certain pests, that their residual activities are sometimes poor and the effects are not satisfactorily maintained for a certain period of time, and that satisfactory pesticidal effects can not be practically achieved depending on applications. Also, even if there are some pesticides excellent in their pesticidal effects, they are demanded to be improved in respect of safety to fishes, crustacea and domestic animals and are also demanded to achieve a high pesticidal effect at a small dosage.

Means to Solve the Problem

The present inventors have intensively studied to solve these problems, and as a result of the study, they have discovered that by combining an anthranilamide compound of the following formula (I) or its salt with other pesticide, unexpected effects of killing pests grown in some place by one time and reducing a dosage than in a case of using an active compound respectively alone, can be achieved. The present invention has been accomplished on the basis of this discovery.

That is, the present invention provides a pesticidal composition comprising synergistically effective amounts of at least one anthranilamide compound represented by the formula (I) or its salt and other pesticide:

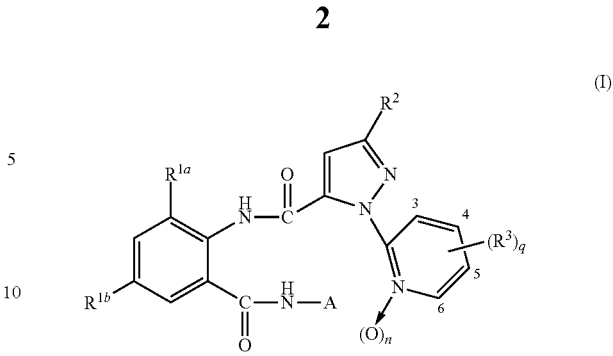

wherein each of $R^{1a}$ and $R^{1b}$ which are independent of each other, is halogen; each of $R^2$ and $R^3$ is halogen, alkyl, haloalkyl, alkoxy, haloalkoxy or cyano; A is alkyl substituted by Y; Y is $C_{3-4}$ cycloalkyl which may be substituted by at least one substituent selected from the group consisting of halogen, alkyl and haloalkyl; n is 0 or 1; and q is an integer of from 0 to 4; provided that $R^{1a}$ and $R^{1b}$ are not simultaneously chlorine nor bromine. The present invention further provides a method for controlling pests by applying synergistically effective amounts of the above anthranilamide compound or its salt and other pesticide.

In the above formula (I), the number of substituents Y in A may be 1 or more, and if more, the respective substituents Y may be the same or different. Further, the positions for substitution of the substituents Y may be any positions. The number of substituents Y in A is preferably 1.

The number of halogen, alkyl or haloalkyl as the substituent for the $C_{3-4}$ cycloalkyl in Y, may be 1 or more, and if more, the respective substituents may be the same or different. Further, the positions for substitution for the respective substituents may be any positions. The $C_{3-4}$ cycloalkyl in Y is preferably unsubstituted, or when it has the above substituents, the number of such substituents is preferably from 1 to 5.

As the halogen or halogen as the substituent in $R^{1a}$, $R^{1b}$, $R^2$, $R^3$ or Y, an atom of fluorine, chlorine, bromine or iodine may be mentioned. The number of halogens as substituents may be 1 or more, and if more, the respective halogens may be the same or different. Further, the positions for substitution of such halogens may be any positions.

In the above formula (I), the alkyl or alkyl moiety in $R^2$, $R^3$, A or Y may be linear or branched. As its specific example, $C_{1-6}$ alkyl such as methyl, ethyl, propyl, isopropyl, butyl, tert-butyl, pentyl or hexyl may be mentioned.

As a specific example of the $C_{3-4}$ cycloalkyl or cycloalkyl moiety in Y, cyclopropyl or cyclobutyl may be mentioned, and cyclopropyl is particularly preferred.

The salt of the anthranilamide compound of the above formula (I) includes all kinds so long as they are agriculturally acceptable. For example, an alkali metal salt such as a sodium salt or a potassium salt; an alkaline earth metal salt such as a magnesium salt or a calcium salt; an ammonium salt such as a dimethylammonium salt or a triethylammonium salt; an inorganic acid salt such as a hydrochloride, a perchlorate, a sulfate or a nitrate; or an organic acid salt such as an acetate or a methanesulfonate, may be mentioned.

The anthranilamide compound of the formula (I) may have optical isomers or geometrical isomers, and such isomers and mixtures thereof are both included in the present invention. Further, in the present invention, various isomers other than those mentioned above, may be included within the scope of the common knowledge in this technical field. Further, depending upon the type of such an isomer, the chemical structure may be different from the above-mentioned formula (I), but it is obvious to one skilled in the art that such a structure is in isomeric relation and thus falls within the scope of the present invention.

The anthranilamide compound of the above formula (I) or its salt can be obtained by the method disclosed in Patent Document 1.

Effects of the Invention

The pesticidal composition of the present invention has a stably high pesticidal effect against pests, and pests can be controlled by this composition.

BEST MODE FOR CARRYING OUT THE INVENTION

Now, some of anthranilamide compounds of the formula (I) or their salts preferred as an active compound in the pesticidal composition of the present invention are exemplified below, but the present invention is by no means restricted thereto.

(1) A compound of the above formula (I) wherein $R^{1b}$ is fluorine or chlorine.
(2) A compound of the above formula (I) wherein $R^{1b}$ is chlorine.
(3) A compound of the above formula (I) wherein $R^2$ is halogen, haloalkyl or haloalkoxy.
(4) A compound of the above formula (I) wherein $R^3$ is halogen.
(5) A compound of the above formula (I) wherein $R^3$ is halogen and 3- or 5-monosubstituted, or 3,5-disubstituted.
(6) A compound of the above formula (I) wherein Y is cyclopropyl.
(7) A compound of the above formula (I) wherein Y is cyclopropyl, and such cyclopropyl is substituted by 1 to 5 substituents selected from the group consisting of halogen, alkyl and haloalkyl.
(8) A compound of the above formula (I) wherein $R^2$ is halogen, haloalkyl or haloalkoxy, $R^3$ is halogen or haloalkyl, A is alkyl substituted by Y, Y is cyclopropyl which may be substituted by at least one substituent selected from the group consisting of halogen and alkyl, n is 0, and q is 1.
(9) A compound as defined in the above (8), wherein $R^3$ is 3-monosubstituted.
(10) A compound of the above formula (I) wherein $R^2$ is halogen, haloalkyl or haloalkoxy, $R^3$ is halogen, A is alkyl substituted by Y, Y is cyclopropyl, n is 0, and q is 1.
(11) A compound as defined in the above (10), wherein $R^3$ is 3-monosubstituted.
(12) A compound as defined in the above (11) wherein $R^{1b}$ is chlorine.
(13) A compound of the formula (I) which is represented by the formula (I-1):

(I-1)

wherein $R^{1a}$ is bromine, $R^{1b}$ is fluorine or chlorine, $R^2$ is halogen, haloalkyl or haloalkoxy, $R^{3a}$ is halogen or haloalkyl, each of $R^{3b}$, $R^{3c}$ and $R^{3d}$ is a hydrogen atom, A is alkyl substituted by Y, Y is cyclopropyl which may be substituted by 1 to 5 substituents selected from the group consisting of halogen, alkyl and haloalkyl.

(14) A compound as defined in the above (13) wherein Y is cyclopropyl.
(15) A compound of the formula (I) which is represented by the formula (Ia):

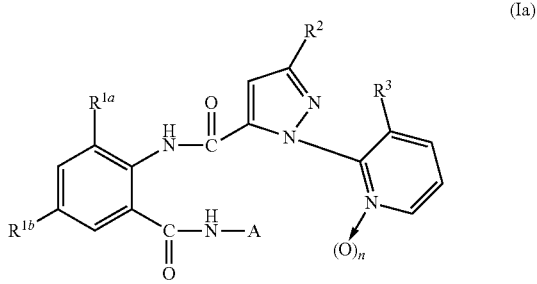

(Ia)

wherein $R^{1a}$ is bromine, $R^{1b}$ is fluorine or chlorine, each of $R^2$ and $R^3$ is halogen or —$CF_3$, A is alkyl substituted by Y, Y is $C_{3-4}$ cycloalkyl which may be substituted by halogen or alkyl, and n is 0 or 1.

(16) A compound of the formula (I) which is represented by the above formula (Ia), wherein $R^{1b}$ is fluorine or chlorine, each of $R^2$ and $R^3$ is halogen or —$CF_3$, A is —X-Y, X is alkylene, Y is $C_{3-4}$ cycloalkyl which may be substituted by halogen or alkyl, and n is 0 or 1.
(17) A compound of the formula (I) which is represented by the above formula (Ia), wherein $R^{1b}$ is fluorine or chlorine, each of $R^2$ and $R^3$ is halogen or —$CF_3$, A is —X-Y, X is alkylene, Y is cyclopropyl, and n is 0 or 1.
(18) A compound as defined in the above (17) wherein $R^{1b}$ is chlorine.
(19) A compound as defined in the above (17) wherein $R^{1b}$ is fluorine.
(20) At least one compound selected from the group consisting of N-[2-bromo-4-chloro-6-[[α-methyl-(cyclopropylmethyl)amino]carbonyl]-phenyl]-3-bromo-1-(3-chloro-2-pyridyl)-1H-pyrazole-5-carboxamide (Compound No. 1), N-[2-bromo-4-chloro-6-[[(cyclopropylmethyl)amino]carbonyl]-phenyl]-3-bromo-1-(3-chloro-2-pyridyl)-1H-pyrazole-5-carboxamide (compound No. 2) and N-[2-bromo-4-fluoro-6-[[α-methyl-(cyclopropylmethyl)amino]carbonyl]-phenyl]-3-bromo-1-(3-chloro-2-pyridyl)-1H-pyrazole-5-carboxamide (Compound No. 3).
(21) N-[2-bromo-4-chloro-6-[[α-methyl-(cyclopropylmethyl)amino]carbonyl]-phenyl]-3-bromo-1-(3-chloro-2-pyridyl)-1H-pyrazole-5-carboxamide.
(22) N-[2-bromo-4-chloro-6-[[(cyclopropylmethyl)amino]carbonyl]-phenyl]-3-bromo-1-(3-chloro-2-pyridyl)-1H-pyrazole-5-carboxamide.
(23) N-[2-bromo-4-fluoro-6-[[(α-methyl-(cyclopropylmethyl)amino]carbonyl]-phenyl]-3-bromo-1-(3-chloro-2-pyridyl)-1H-pyrazole-5-carboxamide.

In the present invention, as other pesticide to be combined with the compound of the formula (I) or its salt, an insecticide and/or a fungicide may be mentioned.

Preferred compounds as the insecticide are exemplified below.

(A) Organophosphorus Compounds
(A-1) profenofos
(A-2) dichlorvos (A-3) fenamiphos
(A-4) fenitrothion
(A-5) EPN
(A-6) diazinon
(A-7) chlorpyrifos
(A-8) acephate
(A-9) prothiofos
(A-10) fosthiazate
(A-11) cadusafos
(A-12) dislufoton
(A-13) isoxathion
(A-14) isofenphos
(A-15) ethion
(A-16) etrimfos
(A-17) quinalphos
(A-18) dimethylvinphos
(A-19) dimethoate
(A-20) sulprofos
(A-21) thiometon
(A-22) vamidothion
(A-23) pyraclofos
(A-24) pyridaphenthion
(A-25) pirimiphos-methyl
(A-26) propaphos
(A-27) phosalone
(A-28) formothion
(A-29) malathion
(A-30) tetrachlovinphos
(A-31) chlorfenvinphos
(A-32) cyanophos
(A-33) trichlorfon
(A-34) methidathion
(A-35) phenthoate
(A-36) ESP
(A-37) azinphos-methyl
(A-38) fenthion
(A-39) heptenophos
(A-40) methoxychlor
(A-41) parathion
(A-42) phosphocarb
(A-43) demeton-S-methyl
(A-44) monocrotophos
(A-45) methamidophos
(A-46) imicyafos
(A-47) parathion-methyl
(A-48) terbufos
(A-49) phosphamidon
(A-50) phosmet
(A-51) phorate
(A-52) chlorpyrifos-methyl
(B) Carbamate Compounds
(B-1) carbaryl
(B-2) propoxur
(B-3) aldicarb
(B-4) carbofuran
(B-5) thiodicarb
(B-6) methomyl
(B-7) Oxamyl
(B-8) ethiofencarb
(B-9) pirimicarb
(B-10) fenobucarb
(B-11) carbosulfan
(B-12) benfuracarb
(B-13) bendiocarb
(B-14) furathiocarb
(B-15) isoprocarb
(B-16) metolcarb
(B-17) xylylcarb
(B-18) XMC
(B-19) fenothiocarb
(C) Pyrethroid Compounds
(C-1) fenvalerate
(C-2) permethrin
(C-3) cypermethrin
(C-4) deltamethrin
(C-5) cyhalothrin
(C-6) tefluthrin
(C-7) ethofenprox
(C-8) cyfluthrin
(C-9) fenpropathrin
(C-10) flucythrinate
(C-11) fluvalinate
(C-12) cycloprothrin
(C-13) lambda-cyhalothrin
(C-14) pyrethrin
(C-15) esfenvalerate
(C-16) tetramethrin
(C-17) resmethrin
(C-18) protrifenbute
(C-19) bifenthrin
(C-20) zeta-cypermethrin
(C-21) acrinathrin
(C-22) alpha-cypermethrin
(C-23) allethrin
(C-24) gamma-cyhalothrin
(C-25) theta-cypermethrin
(C-26) tau-fluvalinate
(C-27) tralomethrin
(C-28) profluthrin
(C-29) beta-cypermethrin
(C-30) beta-cyfluthrin
(C-31) metofluthrin
(C-32) phenothrin
(D) Neonicotinoid Compounds
(D-1) imidacloprid
(D-2) nitenpyram
(D-3) acetamiprid
(D-4) thiacloprid
(D-5) thiamethoxam
(D-6) clothianidin
(D-7) dinotefuran
(D-8) nithiazine
(E) Benzoylurea Compounds
(E-1) diflubenzuron
(E-2) chlorfluazuron
(E-3) teflubenzuron
(E-4) flufenoxuron
(E-5) triflumuron
(E-6) hexaflumuron
(E-7) lufenuron
(E-8) novaluron
(E-9) noviflumuron
(E-10) bistrifluoron
(E-11) fluazuron
(F) Nereistoxin Derivatives
(F-1) cartap
(F-2) thiocyclam
(F-3) bensultap
(F-4) thiosultap-sodium
(G) Hydrazine Compounds
(G-1) tebufenozide
(G-2) chlomafenozide
(G-3) methoxyfenozide
(G-4) halofenizide (H) Juvenile Hormone-Like Compounds
(H-1) methoprene
(H-2) pyriproxyfen
(H-3) fenoxycarb
(H-4) diofenolan
(I) Antibiotics and Semisynthetic Antibiotics
(I-1) spinosad
(I-2) emamectin-benzoate
(I-3) avermectin
(I-4) milbemectin
(I-5) ivermectin
(I-6) lepimectin
(I-7) DE-175 (spinetoram)
(I-8) abamectin
(I-9) emamectin
(J) Pyrrole Compounds
(J-1) chlorfenapyr
(K) Thiadiazine Compounds
(K-1) buprofezin
(L) Silane Compounds
(L-1) silafluofen
(M) Organochlorine Compounds
(M-1) dicofol
(M-2) tetradifon
(M-3) endosulfan
(M-4) dienochlor
(M-5) dieldrin
(N) Pyrazole Compounds
(N-1) fenpyroximate
(N-2) fipronil
(N-3) tebufenpyrad
(N-4) ethiprole
(N-5) tolfenpyrad
(N-6) acetoprole
(N-7) pyrafluprole
(N-8) pyriprole
(O) Organotin Compounds
(O-1) fenbutatin oxide
(O-2) cyhexatin
(P) Natural Products
(P-1) azadirachtin
(P-2) rotenone
(Q) Microbial Pesticides
(Q-1) *Bacillus thuringienses aizawai*
(Q-2) *Bacillus thuringienses kurstaki*
(Q-3) *Bacillus thuringienses israelensis*
(Q-4) *Bacillus thuringienses japonensis*
(Q-5) *Bacillus thuringienses tenebrionis*
(Q-6) insecticidal crystal protein produced by *Bacillus thuringienses*
(Q-7) insect viruses
(Q-8) baculovirus
(Q-9) entomopathogenic fungi
(Q-10) nematophagous fungi
(R) Repellents
(R-1) deet
(S) Insecticides not Included in the Above (A) to (R)
(S-1) flonicamid
(S-2) hexythiazox
(S-3) amitraz
(S-4) chlordimeform
(S-5) triazamate
(S-6) pymetrozine
(S-7) pyrimidifen
(S-8) indoxacarb
(S-9) acequinocyl
(S-10) etoxazole
(S-11) cyromazine
(S-12) 1,3-dichloropropene
(S-13) diafenthiuron
(S-14) benclothiaz
(S-15) flufenerim
(S-16) pyridalyl
(S-17) spiromesifen
(S-18) spirotetramat
(S-19) propargite
(S-20) clofentezine
(S-21) metaflumizone
(S-22) flubendiamide
(S-23) cyflumetofen
(S-24) chlorantraniliprole
(S-25) cyenopyrafen
(S-26) pyrifluquinazon
(S-27) fenazaquin
(S-28) pyridaben
(S-29) fluacrypyrim
(S-30) spirodiclofen
(S-31) bifenazate
(S-32) amidoflumet
(S-33) chlorobenzoate
(S-34) sulfluramid
(S-35) hydramethylnon
(S-36) metaldehyde
(S-37) ryanodine
(S-38) HGW-86

Some of more preferred insecticides to be used as an active compound of the pesticidal composition of the present invention are described below.

(1) At least one member selected from the group consisting of organophosphorus compounds, carbamate compounds, pyrethroid compounds, neonicotinoid compounds, benzoylurea compounds, nereistoxin derivatives, hydrazine compounds, juvenile hormone-like compounds, antibiotics, semisynthetic antibiotics, pyrrole compounds, thiadiazine compounds, silane compounds, organochlorine compounds, pyrazole compounds, organotin compounds, natural products, microbial pesticides, repellents, flonicamid, hexythiazox, amitraz, chlordimeform, triazamate, pymetrozine, pyrimidifen, indoxacarb, acequinocyl, etoxazole, cyromazine, 1,3-dichloropropene, diafenthiuron, benclothiaz, flufenerim, pyridalyl, spiromesifen, spirotetramat, propargite, clofentezine, metaflumizone, flubendiamide, cyflumetofen, chlorantraniliprole, cyenopyrafen, pyrifluquinazon, fenazaquin, pyridaben, fluacrypyrim, spirodiclofen, bifenazate, amidoflumet, chlorobenzoate, sulfluramid, hydramethylnon, metaldehyde, ryanodine and HGW-86.

(2) At least one member selected from the group consisting of profenofos, dichlorvos, fenamiphos, fenitrothion, EPN, diazinon, chlorpyrifos, acephate, prothiofos, fosthiazate, cadusafos, dislufoton, isoxathion, isofenphos, ethion, etrimfos, quinalphos, dimethylvinphos, dimethoate, sulprofos, thiometon, vamidothion, pyraclofos, pyridaphenthion, pirimiphos-methyl, propaphos, phosalone, formothion, malathion, tetrachlovinphos, chlorfenvinphos, cyanophos, trichlorfon, methidathion, phenthoate, ESP, azinphos-methyl, fenthion, heptenophos, methoxychlor, parathion, phosphocarb, demeton-S-methyl, monocrotophos, methamidophos, imicyafos, parathion-methyl, terbufos, phosphamidon, phosmet, phorate, chlorpyrifos-methyl, carbaryl, propoxur, aldicarb, carbofuran, thiodicarb, methomyl, oxamyl, ethiofencarb, pirimicarb, fenobucarb, carbosulfan, benfuracarb, bendiocarb, furathiocarb, isoprocarb, metolcarb, xylylcarb, XMC, fenothiocarb, fenvalerate, permethrin, cypermethrin, deltamethrin, cyhalothrin, tefluthrin, ethofenprox, cyfluthrin, fenpropathrin, flucythrinate, fluvalinate, cycloprothrin, lambda-cyhalothrin, pyrethrin, esfenvalerate, tetramethrin, resmethrin, protrifenbute, bifenthrin, zeta-cypermethrin, acrinathrin, alpha-cypermethrin, allethrin, gamma-cyhalothrin, theta-cypermethrin, tau-fluvalinate, tralomethrin, profluthrin, beta-cypermethrin, beta-cyfluthrin, metofluthrin, phenothrin, imidacloprid, nitenpyram, acetamiprid, thiacloprid, thiamethoxam, clothianidin, dinotefuran, nithiazine, diflubenzuron, chlorfluazuron, teflubenzuron, flufenoxuron, triflumuron, hexaflumuron, lufenuron, novaluron, noviflumuron, bistrifluoron, fluazuron, cartap, thiocyclam, bensultap, thiosultap-sodium, tebufenozide, chlomafenozide, methoxyfenozide, halofenizide, methoprene, pyriproxyfen, fenoxycarb, diofenolan, spinosad, emamectin-benzoate, avermectin, milbemectin, ivermectin, lepimectin, DE-175, abamectin, emamectin, chlorfenapyr, buprofezin, silafluofen, dicofol, tetradifon, endosulufan, dienochlor, dieldrin, fenpyroximate, fipronil, tebufenpyrad, ethiprole, tolfenpyrad, acetoprole, pyrafluprole, pyriprole, fenbutatin oxide, cyhexatin, azadirachtin, rotenone, *Bacillus thuringienses aizawai, Bacillus thuringienses kurstaki, Bacillus thuringienses israelensis, Bacillus thuringienses japonensis, Bacillus thuringienses tenebrionis*, insecticidal crystal protein produced by *Bacillus thuringienses*, insect viruses, baculovirus, etomobathogenic fungi, nematophagous fungi, deet, flonicamid, hexythiazox, amitraz, chlordimeform, triazamate, pymetrozine, pyrimidifen, indoxacarb, acequinocyl, etoxazole, cyromazine, 1,3-dichloropropene, diafenthiuron, benclothiaz, flufenerim, pyridalyl, spiromesifen, spirotetramat, propargite, clofentezine, metaflumizone, flubendiamide, cyflumetofen, chlorantraniliprole, cyenopyrafen, pyrifluquinazon, fenazaquin, pyridaben, fluacrypyrim, spirodiclofen, bifenazate, amidoflumet, chlorobenzoate, sulfluramid, hydramethylnon, metaldehyde, ryanodine and HGW-86.

(3) At least one member selected from the group consisting of organophosphorus compounds, pyrethroid compounds, neonicotinoid compounds, benzoylurea compounds, hydrazine compounds, antibiotics, semisynthetic antibiotics, pyrrole compounds, pyrazole compounds, organotin compounds, natural products, flonicamid, amitraz, acequinocyl, cyromazine, pyridalyl, propargite, pypriflu-quinazon and pyridaben.

(4) At least one member selected from the group consisting of profenofos, dichlorvos, fenamiphos, fenitrothion, EPN, diazinon, chlorpyrifos, acephate, prothiofos, fosthiazate, cadusafos, dislufoton, isoxathion, isofenphos, ethion, etrimfos, quinalphos, dimethylvinphos, dimethoate, sulprofos, thiometon, vamidothion, pyraclofos, pyridaphenthion, pirimiphos-methyl, propaphos, phosalone, formothion, malathion, tetrachlovinphos, chlorfenvinphos, cyanophos, trichlorfon, methidathion, phenthoate, ESP, azinphos-methyl, fenthion, heptenophos, methoxychlor, parathion, phosphocarb, demeton-S-methyl, monocrotophos, methamidophos, imicyafos, parathion-methyl, terbufos, phosphamidon, phosmet, phorate, chlorpyrifos-methyl, fenvalerate, permethrin, cypermethrin, deltamethrin, cyhalothrin, tefluthrin, ethofenprox, cyfluthrin, fenpropathrin, flucythrinate, fluvalinate, cycloprothrin, lambda-cyhalothrin, pyrethrin, esfenvalerate, tetramethrin, resmethrin, protrifenbute, bifenthrin, zeta-cypermethrin, acrinathrin, alpha-cypermethrin, allethrin, gamma-cyhalothrin, theta-cypermethrin, tau-fluvalinate, tralomethrin, profluthrin, beta-cypermethrin, beta-cyfluthrin, metofluthrin, phenothrin, imidacloprid, nitenpyram, acetamiprid, thiacloprid, thiamethoxam, clothianidin, dinotefuran, nithiazine, diflubenzuron, chlorfluazuron, teflubenzuron, flufenoxuron, triflumuron, hexaflumuron, lufenuron, novaluron, noviflumuron, bistrifluoron, fluazuron, tebufenozide, chlomafenozide, methoxyfenozide, halofenizide, spinosad, emamectin-benzoate, avermectin, milbemectin, ivermectin, lepimectin, DE-175, abamectin, emamectin, chlorfenapyr, fenpyroximate, fipronil, tebufenpyrad, ethiprole, tolfenpyrad, acetoprole, pyrafluprole, pyriprole, fenbutatin oxide, cyhexatin, azadirachtin, rotenone, flonicamid, amitraz, acequinocyl, cyromazine, pyridalyl, propargite, pyrifluquinazon and pyridaben.

(5) At least one member selected from the group consisting of fosthiazate, permethrin, deltamethrin, bifenthrin, zeta-cypermethrin, phenothrin, imidacloprid, acetamiprid, thiacloprid, clothianidin, dinotefuran, chlorfluazuron, flufenoxuron, lufenuron, tebufenozide, spinosad, emamectin-benzoate, chlorfenapyr, fipronil, fenbutatin oxide, azadirachtin, flonicamid, amitraz, acequinocyl, cyromazine, pyridalyl, propargite, pyrifluquinazon and pyridaben.

(6) At least one member selected from the group consisting of fosthiazate, deltamethrin, bifenthrin, zeta-cypermethrin, phenothrin, imidacloprid, acetamiprid, thiacloprid, clothianidin, dinotefuran, chlorfluazuron, flufenoxuron, tebufenozide, spinosad, emamectin-benzoate, chlorfenapyr, fipronil, fenbutatin oxide, azadirachtin, flonicamid, acequinocyl, cyromazine, pyridalyl, propargite, pyrifluquinazon and pyridaben.

(7) At least one member selected from the group consisting of fosthiazate, bifenthrin, imidacloprid, acetamiprid, thiacloprid, clothianidin, dinotefuran, chlorfluazuron, spinosad, emamectin-benzoate, fenbutatin oxide, azadirachtin, flonicamid, pyridalyl and pyridaben.

In the present invention, preferred compounds as the fungicide to be combined with the compound of the formula (I) or its salt are described below.

[1] Pyrimidinamine Compounds
[1-1] mepanipyrim
[1-2] pyrimethanil
[1-3] cyprodinil
[2] Pyridinamine Compounds
[2-1] fluazinam
[3] Azole Compounds
[3-1] triadimefon
[3-2] bitertanol
[3-3] triflumizole
[3-4] etaconazole
[3-5] propiconazole
[3-6] penconazole
[3-7] flusilazole
[3-8] myclobutanil
[3-9] cyproconazole
[3-10] tebuconazole
[3-11] hexaconazole
[3-12] furconazole-cis
[3-13] prochloraz
[3-14] metconazole
[3-15] epoxiconazole
[3-16] tetraconazole
[3-17] oxpoconazole fumarate
[3-18] sipconazole
[3-19] prothioconazole
[3-20] triadimenol
[3-21] flutriafol
[3-22] difenoconazole

[3-23] fluquinconazole
[3-24] fenbuconazole
[3-25] bromuconazole
[3-26] diniconazole
[3-27] tricyclazole
[3-28] probenazole
[3-29] simeconazole
[3-30] pefurazoate
[3-31] ipconazole
[3-32] imibenconazole
[4] Quinoxaline Compounds
[4-1] quinomethionate
[5] Dithiocarbamate Compounds
[5-1] maneb
[5-2] zineb
[5-3] mancozeb
[5-4] polycarbamate
[5-5] metiram
[5-6] propineb
[5-7] thiram
[6] Organic Chlorine Compounds
[6-1] fthalide
[6-2] chlorothalonil
[6-3] quintozene
[7] Imidazole Compounds
[7-1] benomyl
[7-2] thiophanate-Methyl
[7-3] carbendazim
[7-4] thiabendazole
[7-5] fuberiazole
[7-6] cyazofamid
[8] Cyanoacetamide Compounds
[8-1] cymoxanil
[9] Phenylamide compounds
[9-1] metalaxyl
[9-2] metalaxyl-M
[9-3] mefenoxam
[9-4] oxadixyl
[9-5] ofurace
[9-6] benalaxyl
[9-7] benalaxyl-M (another name: kiralaxyl, chiralaxyl)
[9-8] furalaxyl
[9-9] cyprofuram
[10] Sulfenic Acid Compounds
[10-1] dichlofluanid
[11] Copper Compounds
[11-1] cupric hydroxide
[11-2] oxine copper
[12] Isoxazole Compounds
[12-1] hymexazol
[13] Organophosphorus Compounds
[13-1] fosetyl-Al
[13-2] tolcofos-methyl
[13-3] edifenphos
[13-4] iprobenfos
[13-5] S-benzyl O,O-diisopropylphosphorothioate
[13-6] O-ethyl S,S-diphenylphosphorodithioate
[13-7] aluminumethylhydrogene phosphonate
[14] N-Halogenothioalkyl Compounds
[14-1] captan
[14-2] captafol
[14-3] folpet
[15] Dicarboximide Compounds
[15-1] procymidone
[15-2] iprodione
[15-3] vinclozolin
[16] Benzanilide Compounds
[16-1] flutolanil
[16-2] mepronil
[16-3] zoxamid
[16-4] tiadinil
[17] Anilide Compounds
[17-1] carboxin
[17-2] oxycarboxin
[17-3] thifluzamide
[17-4] MTF-753 (penthiopyrad)
[17-5] boscalid
[18] Piperazine Compounds
[18-1] triforine
[19] Pyridine Compounds
[19-1] pyrifenox
[20] Carbinol Compounds
[20-1] fenarimol
[20-2] flutriafol
[21] Pepridine Compounds
[21-1] fenpropidine
[22] Morpholine Compounds
[22-1] fenpropimorph
[22-2] spiroxamine
[22-3] tridemorph
[23] Organotin Compounds
[23-1] fentin Hydroxide
[23-2] fentin Acetate
[24] Urea Compounds
[24-1] pencycuron
[25] Cinnamic Acid Compounds
[25-1] dimethomorph
[25-2] flumorph
[26] Phenylcarbamate Compounds
[26-1] diethofencarb
[27] Cyanopyrrole Compounds
[27-1] fludioxonil
[27-2] fenpiclonil
[28] Strobilurin Compounds
[28-1] azoxystrobin
[28-2] kresoxim-methyl
[28-3] metominofen
[28-4] trifloxystrobin
[28-5] picoxystrobin
[28-6] oryzastrobin
[28-7] dimoxystrobin
[28-8] pyraclostrobin
[28-9] fluoxastrobin
[29] Oxazolidinone Compounds
[29-1] famoxadone
[30] Thiazole Carboxamide Compounds
[30-1] ethaboxam
[31] Silyl Amide Compounds
[31-1] silthiopham
[32] Aminoacid Amidecarbamate Compounds
[32-1] iprovalicarb
[32-2] benthiavalicarb-isopropyl
[33] Imidazolidine Compounds
[33-1] fenamidone
[34] Hydroxyanilide Compounds
[34-1] fenhexamid
[35] Benzene Sulfonamide Compounds
[35-1] flusulfamid
[36] Oxime Ether Compounds
[36-1] cyflufenamid
[37] Phenoxyamide Compounds
[37-1] fenoxanil
[38] Anthraquinone Compounds
[39] Crotonic Acid Compounds

[40] Antibiotics
[40-1] validamycin
[40-2] kasugamycin
[40-3] polyoxins
[41] Guanidine Compounds
[41-1] iminoctadine
[42] Other Compounds
[42-1] isoprothiolane
[42-2] pyroquilon
[42-3] diclomezine
[42-4] quinoxyfen
[42-5] propamocarb hydrochloride
[42-6] chloropicrin
[42-7] dazomet
[42-8] metam-sodium
[42-9] nicobifen
[42-10] metrafenone
[42-11] MTF-753
[42-12] UBF-307
[42-13] diclocymet
[42-14] proquinazid
[42-15] amisulbrom (another name: amibromdole)
[42-16] KIF-7767 (KUF-1204, pyribencarb methyl, mepyricarb)
[42-17] Syngenta 446510 (mandipropamid, dipromandamid)
[42-18] carpropamid
[42-19] BCF051
[42-20] BCM061
[42-21] BCM062

Some of more preferred fungicides to be used as an active compound of the pesticidal composition of the present invention are described below.

(1) At least one member selected from the group consisting of pyrimidinamine compounds, pyridinamine compounds, azole compounds, quinoxaline compounds, dithiocarbamate compounds, organic chlorine compounds, imidazole compounds, cyanoacetamide compounds, phenylamide compounds, sulfenic acid compounds, copper compounds, isoxazole compounds, organophosphorus compounds, N-halogenothioalkyl compounds, dicarboximide compounds, benzanilide compounds, anilide compounds, piperazine compounds, pyridine compounds, carbinol compounds, piperidine compounds, morpholine compounds, organotin compounds, urea compounds, cinnamic acid compounds, phenylcarbamate compounds, cyanopyrrole compounds, strobilurin compounds, oxazolidinone compounds, thiazole carboxamide compounds, silyl amide compounds, aminoacid amidecarbamate compounds, imidazolidine compounds, hydroxyanilide compounds, benzene sulfonamide compounds, oxime ether compounds, phenoxyamide compounds, anthraquinone compounds, crotonic acid compounds, antibiotics, guanidine compounds, isoprothiolane, pyroquilon, diclomezine, quinoxyfen, propamocarb hydrochloride, chloropicrin, dazomet, metam-sodium, nicobifen, metrafenone, MTF-753, UBF-307, diclocymet, proquinazid, amisulbrom, KIF-7767, Syngenta 446510, carpropamid, BCF051, BCM061 and BCM062.

(2) At least one member selected from the group consisting of mepanipyrim, pyrimethanil, cyprodinil, fluazinam, triadimefon, bitertanol, triflumizole, etaconazole, propiconazole, penconazole, flusilazole, myclobutanil, cyproconazole, tebuconazole, hexaconazole, furconazole-cis, prochloraz, metconazole, epoxiconazole, tetraconazole, oxpoconazole fumarate, sipconazole, prothioconazole, triadimenol, flutriafol, difenoconazole, fluquinconazole, fenbuconazole, bromuconazole, diniconazole, tricyclazole, probenazole, simeconazole, pefurazoate, ipconazole, imibenconazole, quinomethionate, maneb, zineb, mancozeb, polycarbamate, metiram, propineb, thiram, fthalide, chlorothalonil, quintozene, benomyl, thiophanate-Methyl, carbendazim, thiabendazole, fuberiazole, cyazofamid, cymoxanil, metalaxyl, metalaxyl-M, mefenoxam, oxadixyl, ofurace, benalaxyl, benalaxyl-M, furalaxyl, cyprofuram, dichlofluanid, cupric hydroxide, oxine copper, hymexazol, fosetyl-Al, tolcofos-methyl, edifenphos, iprobenfos, S-benzyl O,O-diisopropylphosphorothioate, O-ethyl S,S-diphenylphosphorodithioate, aluminumethylhydrogen phosphonate, captan, captafol, folpet, procymidone, iprodione, vinclozolin, flutolanil, mepronil, zoxamid, tiadinil, carboxin, oxycarboxin, thifluzamide, MTF-753, boscalid, triforine, pyrifenox, fenarimol, flutriafol, fenpropidine, fenpropimorph, spiroxamine, tridemorph, fentin hydroxide, fentin acetate, pencycuron, dimethomorph, flumorph, diethofencarb, fludioxonil, fenpiclonil, azoxystrobin, kresoxim-methyl, metominofen, trifloxystrobin, picoxystrobin, oryzastrobin, dimoxystrobin, pyraclostrobin, fluoxastrobin, famoxadone, ethaboxam, silthiopham, iprovalicarb, benthiavalicarb-isopropyl, fenamidone, fenhexamid, flusulfamid, cyflufenamid, fenoxanil, anthraquinone compounds, crotonic acid compounds, validamycin, kasugamycin, polyoxins, iminoctadine, isoprothiolane, pyroquilon, diclomezine, quinoxyfen, propamocarb hydrochloride, chloropicrin, dazomet, metam-sodium, nicobifen, metrafenone, MTF-753, UBF-307, diclocymet, proquinazid, amisulbrom, KIF-7767, Syngenta 446510, carpropamid, BCF051, BCM061 and BCM062.

(3) At least one member selected from the group consisting of azole compounds, organic chorine compound, benzanilide compounds, urea compounds, strobilurin compound, antibiotics, isoprothiolane, pyroquilon, diclomezine, diclocymet and carpropamid.

(4) At least one member selected from the group consisting of tricyclazole, probenazole, fthalide, flutolanil, mepronil, tiadinil, pencycuron, azoxystrobin, validamycin, kasugamycin, isoprothiolane, pyroquilon, diclomezine, diclocymet and carpropamid.

Preferred embodiments of the pesticidal compositions of the present invention are described below. The compositions of the present invention are particularly useful, for example, as agents for controlling various pests which become problematic in the agricultural and horticultural fields, i.e. agricultural and horticultural pesticides, agents for controlling sanitary insect pests which are sanitarily harmful to the human, i.e. control agents against sanitary insect pests, agents for controlling pests harmful to trees and turf, i.e. control agents against pests on trees and turf, agents for controlling pests harmful to clothes and household goods, i.e. control agents against clothes and household goods insect pests, and agents for controlling pests which are parasitic on animals i.e. pesticides against parasites on animals.

The agricultural and horticultural pesticides are useful as an insecticide, a miticide, a nematicide, a soil pesticide and a fungicide, and they are effective for controlling plant parasitic mites such as two-spotted spider mite (*Tetranychus urticae*), carmine spider mite (*Tetranychus cinnabarinus*), kanzawa spider mite (*Tetranychus kanzawai*), citrus red mite (*Panonychus citri*), European red mite (*Panonychus ulmi*), broad mite (*Polyphagotarsonemus latus*), pink citrus rust mite (*Aculops pelekassi*) and bulb mite (*Rhizoglyphus echinopus*); agricultural insect pests such as diamondback moth (*Plutella xylostella*), cabbage armyworm (*Mamestra brassicae*), common cutworm (*Spodoptera litura*), codling moth (*Laspeyresia*

*pomonella*), bollworm (*Heliothis zea*), tobacco budworm (*Heliothis virescens*), gypsy moth (*Lymantria dispar*), rice leafroller (*Cnaphalocrocis medinalis*), smaller tea tortrix (*Adoxophyes* sp.), summer fruit tortrix (*Adoxophyes orana fasciata*), peach fruit moth (*Carposina niponensis*), oriental fruit moth (*Grapholita molesta*), black cutworm (*Agrotis ipsilon*), cutworm (*Agrotis segetum*), colorado potato beetle (*Leptinotarsa decemlineata*), cucurbit leaf beetle (*Aulacophora femoralis*), boll weevil (*Anthonomus grandis*), aphids, planthoppers, leafhoppers, scales, bugs, whiteflies, thrips, grasshoppers, anthomyiid flies, scarabs, ants, leafminer flies; plant parasitic nematodes such as root-knot nematodes, cyst nematodes, root-lesion nematodes, rice white-tip nematode (*Aphelenchoides besseyi*), strawberry bud nematode (*Nothotylenchus acris*), pine wood nematode (*Bursaphelenchus xylophilus*); gastropods such as slugs and snails; soil pests such as isopods such as pillbugs (*Armadilidium vulgare*) and pillbugs (*Porcellio scaber*); stored grain insect pests such as angoumois grai moth (*Sitotroga cerealella*), adzuki bean weevil (*Callosobruchus chinensis*), red flour beetle (*Tribolium castaneum*) and mealworms.

Further, as the fungicides, they are effective for controlling diseases such as blast, brown spot or sheath blight of rice (*Oryza sativa*, etc.); powdery mildew, scab, rust, snow mold, snow blight, loose smut, eye spot, leaf spot or glume blotch of cereals (*Hordeum vulgare, Tricum aestivum*, etc.); melanose or scab of citrus (*Citrus* spp., etc.); blossom blight, powdery mildew, *Alternaria* leaf spot or scab of apple (*Malus pumila*); scab or black spot of pear (*Pyrus serotina, Pyrus ussuriensis, Pyrus communis*); brown rot, scab or *Phomopsis* rot of peach (*Prunus persica*, etc.); anthracnose, ripe-rot, powdery mildew or downy mildew of grape (*Vitis vinifera* spp., etc.); anthracnose or brown stem rot of Japanese persimmon (*Diospyros kaki*, etc.); anthracnose, powdery mildew, gummy stem blight or downy mildew of cucurbit (*Cucumis melo*, etc.); early blight, leaf mold or late blight of tomato (*Lycopersicon esculentum*); various *Alternaria* disease pathogens of cruciferous vegetables (*Brassica* sp., *Raphanus* sp., etc); late blight or early blight of potato (*Solanum tuberosum*); powdery mildew of strawberry (*Fragaria*, etc.); and gray mold or disease caused by *Sclerotinia* of various crops; and controlling soil diseases caused by plant pathogens such as *Fusarium, Pythium, Rhizoctonia, Verticillium* and *Plasmodiophora*. As the controlling agents against sanitary insect pests, they are effective for controlling insects which carry pathogen to infect human with diseases, such as *Culex tritaenitorhynchus, Aedes aegypti, Anopheles, Aedes albopictus, Anopheles sinensis, Aedes togoi, Mansonia, Aedes, Phlebotominae, Agriosphodrus*, tsetse fly (*Glossina*), house mosquito (*Culex pipiens*), tropical rat mite (*Ornithonyssus bacoti*), housefly (*Musca domestica*), cockroaches, *Simulium, Chrysops*, flea (*Siphonaptera*), tick (*Ixodoidea*), *Trombiculidae* and louse (*Anoplura*), insects which directly harm human by blood sucking, biting or the like, such as hornet (*Vespinae*), paper wasp (*Polistes*) and *Lymantriidae*; nuisances such as ant (*Formicidae*), rough woodlouse (*Porcellio scaber*), spider (*Araneae*), pillbugs (*Armadilidium vulgare*), centipede (*Chilopada*), millipede (*Diplopada*) and *Thereuonema tuberculate*; and domestic mites which causes alergtic diseases, such as mold mite (*Tyrophagus putrescentiae*), *Dormatophagoides farinae* and *Chelacaropsis moorei*. As the control agents against pests on trees and turf, they are effective for controlling trees pests such as *Bursaphelenchus xylophilus, Monochamus alternatus, Lymantria dispar, Monema flavescens, Hyphantria cunea*, bagworm (*Psychidae*), *Ceroplastes, Coccoidea, Stephanitis pyrioides* and *Dendrolimus spectabilis*; and pests against turf such as *Scarabaeidae*, *Spodoptera depravata, Parapediasia teterrella*, hunting billbug (*Sphenophorus venatus*) and *Gryllotalpidae*. Further, as the control agents against clothes and household goods insect pests, they are effective for controlling case making clothes moth (*Tinea pellionella*), black carpet beetle (*Anthrenus scrophularidae*) and termite (*Rhinotermitidae*). Among them, the agricultural and horticultural pesticides are particularly effective for controlling plant parasitic mites, agricultural insect pests, plant parasitic nematodes, various diseases or the like. Further, they are effective against insect pests having acquired resistance to organophosphorus, carbamate and/or synthetic pyrethroid insecticides. Moreover, the compounds of the formula (I) have excellent systemic properties, and by the application of the compounds of the formula (I) to soil treatment, not only noxious insects, noxious mites, noxious nematodes, noxious gastropods and noxious isopods in soil but also foliage pests can be controlled.

The pesticides against parasites on animals are effective for controlling e.g. external parasites which are parasitic on the body surface of host animals (such as the back, the axilla, the lower abdomen or inside of the thigh) or internal parasites which are parasitic in the body of host animals (such as the stomach, the intestinal tract, the lung, the heart, the liver, the blood vessels, the subcutis or lymphatic tissues), but they are particularly effective for controlling the external parasites.

The external parasites may, for example, be animal parasitic acarina or fleas. Their species are so many that it is difficult to list all of them, and therefore, their typical examples will be given.

The animal parasitic acarina may, for example, be ticks such as *Boophilus microplus, Rhipicephalus sanguineus, Haemaphysalis longicornis, Haemaphysalis flava, Haemaphysalis campanulata, Haemaphysalis concinna, Haemaphysalis japonica, Haemaphysalis kitaokai, Haemaphysalis ias, Ixodes ovatus, Ixodes nipponensis, Ixodes persulcatus, Amblyomma testudinarium, Haemaphysalis megaspinosa, Dermacentor reticulatus*, and *Dermacentor taiwanesis*; common red mite (*Dermanyssus gallinae*); northern fowl mites such as *Ornithonyssus sylviarum*, and *Ornithonyssus bursa*; trombidioids such as *Eutrombicula wichmanni, Leptotrombidium akamushi, Leptotrombidium pallidum, Leptotrombidium fuji, Leptotrombidium tosa, Neotrombicula autumnalis, Eutrombicula alfreddugesi*, and *Helenicula miyagawai*; cheyletidae such as *Cheyletiella yasguri, Cheyletiella parasitivorax*, and *Cheyletiella blakei*; sarcoptic mange mites such as *Psoroptes cuniculi, Chorioptes bovis, Otodectes cynotis, Sarcoptes scabiei*, and *Notoedres cati*; and Demodicidae such as *Demodex canis*. The pesticides against parasites on animals, are particularly effective for the control of ticks among them.

The fleas may, for example, be externally parasitic wingless insects belonging to *Siphonaptera*, more specifically, fleas belonging to *Pulicidae, Ceratephyllus*, etc. Fleas belonging to *Pulicidae* may, for example, be *Ctenocephalides canis, Ctenocephalides felis, Pulex irritans, Echidnophaga gallinacea, Xenopsylla cheopis, Leptopsylla segnis, Nosopsyllus fasciatus*, and *Monopsyllus anisus*. The pesticides against parasites on animals, are particularly effective for the control of fleas belonging to *Pulicidae*, particularly *Ctenocephalides canis* and *Ctenocephalides felis*, among them.

Other external parasites may, for example, be sucking lice (*Anoplura*) such as shortnosed cattle louse (*Haematopinus eurysternus*), horse sucking louse (*Haematopinus asini*), sheep louse, longnosed cattle louse (*Linognathus vituli*), and head louse (*Pediculus capitis*); biting lice such as dog biting louse (*Trichodectes canis*); and blood-sucking dipterous insects such as horsefly (*Tabanus trigonus*), biting midges (*Culicoides schultzei*), and blackfly (*Simulium ornatum*). Further, the internal parasites may, for example, be nematodes such as lung worms, whipworms (*Trichuris*), tuberous worms, gastric parasites, *ascaris*, and filarioidea; cestoda such as *Spirometra erinacei, Diphyllobothrium latum, Dipylidium caninum, Taenia multiceps, Echinococcus granulosus* and *Echinococcus multilocularis*; trematoda such as *Schistosoma japonicum* and *Fasciola hepatica*; and protozoa such as coccidia, malaria parasites (*Plasmodium malariae*), intestinal sarcocyst, toxoplasma, and cryptosporidium.

The host animals may, for example, be pet animals, domestic animals, and poultry, such as dogs, cats, mice, rats, hamsters, guinea pigs, squirrels, rabbits, ferrets, birds (such as pigeons, parrots, hill mynas, Java sparrows, honey parrots, lovebirds and canaries), cows, horses, pigs, sheep, ducks and chickens. The pesticides against parasites on animals, are particularly effective for the control of pests parasitic on pet animals or domestic animals, especially for the control of external parasites, among them. Among pet animals or domestic animals, they are effective particularly for dogs, cats, cows and horses.

In the present invention, the weight ratio of the active compounds of at least one compound of the formula (I) or its salt to other pesticide is from 1:100,000 to 100,000:1, preferably from 1:40,000 to 40,000:1, more preferably from 1:40,000 to 100:1. The pesticidal composition of the present invention is, in the same manner as conventional agricultural chemicals, formulated together with agricultural adjuvants into an emulsifiable concentrate, a dust, granules, a wettable powder, water-dispersible granules, a suspension concentrate, a soluble concentrate, an aerosol, a paste, etc. That is, the pesticidal composition of the present invention may be formulated by mixing the respective active compounds, or by mixing formulations of the respective active compounds. The ratio of the agricultural adjuvants is from 1 to 99.999 parts by weight based on from 0.001 to 99 parts by weight of the active compounds, preferably from 5 to 99.99 parts by weight based on from 0.01 to 95 parts by weight, more preferably from 20 to 99.99 parts by weight based on from 0.01 to 80 parts by weight. In the actual application of such a formulation, it may be used as it is, or may be diluted to a predetermined concentration with a diluent such as water.

As the agricultural adjuvants, there may be mentioned carriers, emulsifiers, suspending agents, dispersants, extenders, penetrating agents, wetting agents, thickeners, defoaming agents, stabilizers or antifreezing agents. They may be added as the case requires. The carriers may be classified into solid carriers and liquid carriers. As the solid carriers, there may be mentioned powders of animal and plant origin, such as starch, activated carbon, soybean flour, wheat flour, wood powder, fish powder or powdered milk; or mineral powders such as talc, kaolin, bentonite, calcium carbonate, zeolite, diatomaceous earth, white carbon, clay or alumina; sulfur powder; anhydrous sodium sulfate; and the like. As the liquid carriers, there may be mentioned water; alcohols such as methyl alcohol or ethylene glycol; ketones such as acetone, methyl ethyl ketone or N-methyl-2-pyrrolidone; ethers such as dioxane or tetrahydrofuran; aliphatic hydrocarbons such as kerosine, gas oil or the like; aromatic hydrocarbons such as xylene, trimethylbenzene, tetramethylbenzene, cyclohexane or solvent naphtha; halogenated hydrocarbons such as chloroform or chlorobenzene; acid amides such as dimethylformamide; esters such as ethyl acetate or glycerine ester of a fatty acid; nitriles such as acetonitrile; sulfur-containing compounds such as dimethyl sulfoxide; vegetable oils such as soybean oil or corn oil; and the like.

The pesticidal composition of the present invention is applied in an active ingredient concentration of a compound of the formula (I) or its salt of from 0.001 to 100,000 ppm, preferably from 0.005 to 50,000 ppm, more preferably from 0.005 to 20,000 ppm, and in an active ingredient concentration of other pesticide of from 0.0001 to 100,000 ppm, preferably from 0.0025 to 50,000 ppm, more preferably from 0.0025 to 20,000 ppm. The active ingredient concentration may optionally be changed depending upon the formulation, the manner, purpose, timing or place of the application and the condition of the insect pests. For instance, aquatic noxious insects can be controlled by applying a formulation having the above-mentioned concentration to the site of the outbreak, and thus, the concentration of the active ingredient in water is less than the above-mentioned range.

The amount of the application of the active ingredient per unit surface area is usually from about 0.001 to 50,000 g, preferably from 0.005 to 10,000 g, per hectare as an active ingredient of a compound of the formula (I) or its salt, and from about 0.0001 to 50,000, preferably from 0.0025 to 10,000 g, per hectare as an active ingredient of other pesticide. However, in a certain special case, the amount of the application may be outside the above range. Various formulations containing the compounds of the present invention or their diluted compositions may be applied by conventional methods for application which are commonly employed, such as spraying (e.g. spraying, jetting, misting, atomizing, powder or grain scattering or dispersing in water), soil application (e.g. mixing or drenching), surface application (e.g. coating, powdering or covering) or impregnation to obtain poisonous feed. Further, it is possible to feed domestic animals with a food containing the above active ingredient and to control the outbreak or growth of pests, particularly insects pests, with their excrements. Furthermore, the active ingredient may also be applied by a so-called ultra low-volume application method. In this method, the composition may be composed of 100% of the active ingredient.

Further, a compound of the formula (I) or its salt may be mixed with or may be used in combination with other agricultural chemicals, fertilizers or phytotoxicity-reducing agents, whereby synergistic effects or activities may sometimes be obtained. Such other agricultural chemicals include, for example, a herbicide, an antivirus agent, an attractant, a plant hormone and a plant growth regulating agent. Especially, with a pesticidal composition having a compound of the formula (I) or its salt mixed with or used in combination with one or more active compounds of other agricultural chemicals, the application range, the application time, the pesticidal activities, etc. may be improved to preferred directions. Each active compounds may separately be formulated so that they may be mixed for use at the time of application, or they may be formulated together. The present invention includes such a pesticidal composition.

In addition, the agricultural chemicals which may be mixed with or may be used in combination with the compound of the formula (I) or its salt may, for example, be active compounds of herbicides as disclosed in Farm Chemicals Handbook (2002), particularly soil application type.

EXAMPLES

Now, the present invention will be described with reference to Examples, but it should be understood that the present invention is by no means restricted thereto.

First, typical examples and Preparation Examples of the compound of the formula (I) will be described.

Preparation Example 1

Preparation of N-[2-bromo-4-chloro-6-[[α-methyl-(cyclopropylmethyl)amino]carbonyl]-phenyl]-3-bromo-1-(3-chloro-2-pyridyl)-1H-pyrazole-5-carboxamide (Compound No. 1)

1 g of triethylamine was gradually added dropwise to a mixed solution comprising 0.6 g of α-methyl-cyclopropylmethylamine hydrochloride and 40 ml of tetrahydrofuran under cooling with ice, followed by stirring at room temperature for 1 hour. Then, a mixed solution comprising 0.85 g of 2-[3-bromo-1-(3-chloro-2-pyridyl)-1H-pyrazol-5-yl]-6-chloro-8-bromo-4H-3,1-benzoxazin-4-one and 10 ml of tetrahydrofuran was gradually added dropwise. After completion of the dropwise addition, the mixed solution was reacted for 4 hours under reflux. After completion of the reaction, the solvent was distilled off under reduced pressure, and to the residue, ethyl acetate and water were added for extraction. The organic layer was washed with water and a saturated sodium chloride aqueous solution and dried over anhydrous magnesium sulfate. The solvent was distilled off under reduced pressure, and the residue was purified by silica gel column chromatography (eluent: n-hexane/ethyl acetate=1/2) to obtain 0.7 g of the desired product having a melting point of 260.6° C.

Preparation Example 2

Preparation of N-[2-bromo-4-chloro-6-[[(cyclopropylmethyl)amino]carbonyl]-phenyl]-3-bromo-1-(3-chloro-2-pyridyl)-1H-pyrazole-5-carboxamide (Compound No. 2)

The desired product having a melting point of from 196 to 199° C. was obtained in the same manner as in Preparation Example 1 except that cyclopropylmethylamine hydrochloride was used instead of α-methylcyclopropylmethylamine hydrochloride.

Preparation Example 3

Preparation of N-[2-bromo-4-fluoro-6-[[α-methyl-(cyclopropylmethyl)amino]carbonyl]-phenyl]-3-bromo-1-(3-chloro-2-pyridyl)-1H-pyrazole-5-carboxamide (Compound No. 3)

The desired product having a melting point of 219.2° C. was obtained in the same manner as in Preparation Example 1 except that 2-[3-bromo-1-(3-chloro-2-pyridyl)-1H-pyrazol-5-yl]-6-fluoro-8-bromo-4H-3,1-benzoxazin-4-one was used instead of 2-[3-bromo-1-(3-chloro-2-pyridyl)-1H-pyrazol-5-yl]-6-chloro-8-bromo-4H-3,1-benzoxazin-4-one.

Now, Formulation Examples of the pesticidal composition of the present invention will be described below, but the types of the active compounds and the agricultural adjuvants, the weight ratio, the formulation, etc. are not limited to specific Examples.

Formulation Example 1

| | |
|---|---|
| (1) Compound No. 1 | 10 parts by weight |
| (2) Clothianidin | 10 parts by weight |
| (3) Clay | 70 parts by weight |
| (4) White carbon | 5 parts by weight |
| (5) Sodium polycarbonate | 3 parts by weight |
| (6) Sodium alkylnaphthalene sulfonate | 2 parts by weight |

The above components are uniformly mixed to obtain a wettable powder.

Formulation Example 2

| | |
|---|---|
| (1) Compound No. 1 | 2 parts by weight |
| (2) Bifenthrin | 3 parts by weight |
| (3) Talc | 60 parts by weight |
| (4) Calcium carbonate | 34.5 parts by weight |
| (5) Liquid paraffin | 0.5 part by weight |

The above components are uniformly mixed to obtain a dust.

Formulation Example 3

| | |
|---|---|
| (1) Compound No. 1 | 5 parts by weight |
| (2) Flonicamid | 15 parts by weight |
| (3) N,N-Dimethylacetamide | 20 parts by weight |
| (4) Polyoxyethylene tristyrylphenyl ether | 10 parts by weight |
| (5) Calcium dodecylbenzenesulfonate | 2 parts by weight |
| (6) Xylene | 48 parts by weight |

The above components are uniformly mixed and dissolved to obtain an emulsifiable concentrate.

Formulation Example 4

| | |
|---|---|
| (1) Clay | 68 parts by weight |
| (2) Sodium ligninsufonate | 2 parts by weight |
| (3) Polyoxyethylenealkylaryl sulfate | 5 parts by weight |
| (4) White carbon | 25 parts by weight |

A mixture of the above respective components, Compound No. 1 and azadiractin are mixed in a weight ratio of 7:2:1 to obtain a wettable powder.

Formulation Example 5

| | |
|---|---|
| (1) Compound No. 1 | 20 parts by weight |
| (2) Acetamiprid | 30 parts by weight |
| (3) Sodium alkylnaphthalene sulfonate condensed with formaldehyde | 2 parts by weight |
| (4) Silicone oil | 0.2 part by weight |
| (5) Water | 47.8 parts by weight |
| (6) Sodium polycarboxylate | 5 parts by weight |
| (7) Anhydrous sodium sulfate | 42.8 parts by weight |

The above components (1) to (5) are uniformly mixed and pulverized to obtain a base liquid, to which the above components (6) and (7) are added, and the mixture is uniformly mixed, granulated and dried to obtain water-dispersible granules.

Preparation Example 6

| | |
|---|---|
| (1) Compound No. 1 | 3 parts by weight |
| (2) Fosthiazate | 2 parts by weight |
| (3) Polyoxyethylene octyl phenyl ether | 1 part by weight |
| (4) Polyoxyethylene alkyl ether phosphate | 0.1 part by weight |
| (5) Granular calcium carbonate | 93.9 parts by weight |

The above components (1) to (4) are preliminarily uniformly mixed and diluted with a proper amount of acetone, and then the mixture is sprayed onto the component (5), and acetone is removed to obtain granules.

Formulation Example 7

| | |
|---|---|
| (1) Compound No. 1 | 1.5 parts by weight |
| (2) Chlorfluazuron | 1 part by weight |
| (3) N,N-Dimethylacetamide | 2.5 parts by weight |
| (4) Soybean oil | 95.0 parts by weight |

The above components are uniformly mixed and dissolved to obtain an ultra low volume formulation.

Formulation Example 8

| | |
|---|---|
| (1) Compound No. 1 | 5 parts by weight |
| (2) Imidacloprid | 35 parts by weight |
| (3) Potassium polyoxyethylene tristyrylphenyl ether | 4 parts by weight |
| (4) Silicone oil | 0.2 part by weight |
| (5) Xanthan gum | 0.1 part by weight |
| (6) Ethylene glycol | 5 parts by weight |
| (7) Water | 50.7 parts by weight |

The above components are uniformly mixed and pulverized to obtain a water-based suspension concentrate.

Formulation Example 9

| | |
|---|---|
| (1) Compound No. 1 | 5 parts by weight |
| (2) Dinotefuran | 5 parts by weight |
| (3) Diethylene glycol monoethyl ether | 80 parts by weight |
| (4) Polyoxyethylene alkyl ether | 10 parts by weight |

The above components are uniformly mixed to obtain a water-soluble concentrate.

Now, Test Examples will be described below.

Biological Assay

In the following biological assays, an emulsifiable concentrate prepared by uniformly mixing and dissolving Compound No. 1, an emulsifying agent (SORPOL 2806B) and N,N-dimethylacetamide in a ratio of 5:5:90, and a commercially available insecticide or a commercially available fungicide were used. They were diluted to a predetermined concentration with water containing a spreader (Shin-Rinoh 0.04%) and subjected to the test by themselves or as a mixed liquid.

Test Example 1

Test on Controlling Effects Against Common Cutworm (*Spodoptera Litura*)

A leaf segment of cabbage was dipped for about 10 seconds in an insecticidal solution and dried in air. A wet filter paper was laid in a petri dish having a diameter of 9 cm, and the dried leaf segment of cabbage was placed thereon. 10 Second-instar larvae of common cutworm were released therein and after putting a cover, left in a constant temperature chamber at 25° C. with lightening. On the 5th or 6th day after release, dead larvae were counted, and the mortality was calculated by the following equation. Here, the insects that were moribund were counted as dead insects. The test results are shown in Tables 1 to 35.

Mortality(%)={(number of dead insects)/(number of surviving insects+number of dead insects)}×100

Further, the theoretical mortality (%) can be calculated from the colby's formula. When the mortality (%) is higher than the theoretical mortality (%), the pesticidal composition of the present invention has a synergistic effect regarding controlling of pests. The theoretical mortality (%) by the colby's formula are shown in brackets in Tables 1 to 35.

TABLE 1

| Compound No. 1 | Flonicamid (ppm) | | | |
|---|---|---|---|---|
| (ppm) | 100 | 50 | 25 | 0 |
| 0.02 | 100 (100) | 100 (100) | 100 (100) | 100 |
| 0.01 | 100 (10) | 100 (37) | 100 (10) | 10 |
| 0 | 0 | 30 | 0 | |

TABLE 2

| Compound No. 1 | Chlorfluazuron (ppm) | | | |
|---|---|---|---|---|
| (ppm) | 0.01 | 0.005 | 0.0025 | 0 |
| 0.02 | 100 (100) | 100 (100) | 100 (100) | 100 |
| 0.01 | 100 (10) | 100 (10) | 100 (10) | 10 |
| 0 | 0 | 0 | 0 | |

TABLE 3

| Compound No. 1 | Imidacloprid (ppm) | | |
|---|---|---|---|
| (ppm) | 50 | 12.5 | 0 |
| 0.02 | 100 (100) | 100 (100) | 100 |
| 0.01 | 80 (78) | 30 (28) | 10 |
| 0 | 75 | 20 | |

TABLE 4

| Compound No. 1 | Fosthiazate (ppm) | |
|---|---|---|
| (ppm) | 25 | 0 |
| 0.02 | 100 (100) | 100 |
| 0.01 | 90 (89) | 10 |
| 0.005 | 100 (88) | 0 |
| 0 | 88 | |

TABLE 5

| Compound No. 1 (ppm) | Acetamiprid (ppm) | | |
|---|---|---|---|
| | 25 | 12.5 | 0 |
| 0.02 | 100 (100) | 100 (100) | 100 |
| 0.01 | 100 (10) | 60 (0) | 0 |
| 0.005 | 38 (10) | 0 (0) | 0 |
| 0 | 10 | 0 | |

TABLE 6

| Compound No. 1 (ppm) | Dinotefuran (ppm) | | | |
|---|---|---|---|---|
| | 12.5 | 6.2 | 3.1 | 0 |
| 0.02 | 100 (100) | 100 (100) | 100 (100) | 100 |
| 0.01 | 80 (13) | 40 (0) | 14 (0) | 0 |
| 0.005 | 20 (13) | 0 (0) | 13 (0) | 0 |
| 0 | 13 | 0 | 0 | |

TABLE 7

| Compound No. 1 (ppm) | Clothianidin (ppm) | |
|---|---|---|
| | 12.5 | 0 |
| 0.02 | 100 (100) | 100 |
| 0.01 | 100 (96) | 56 |
| 0.005 | 100 (93) | 29 |
| 0 | 90 | |

TABLE 8

| Compound No. 1 (ppm) | Thiacloprid (ppm) | |
|---|---|---|
| | 50.0 | 0 |
| 0.02 | 100 (100) | 100 |
| 0.01 | 100 (86) | 56 |
| 0.005 | 80 (77) | 29 |
| 0 | 67 | |

TABLE 9

| Compound No. 1 (ppm) | fenbutatin oxide (ppm) | |
|---|---|---|
| | 200 | 0 |
| 0.02 | 100 (100) | 100 |
| 0.01 | 30 (10) | 10 |
| 0.005 | 10 (0) | 0 |
| 0 | 0 | |

TABLE 10

| Compound No. 1 (ppm) | Emamectin-benzoate (ppm) | | | |
|---|---|---|---|---|
| | 0.01 | 0.005 | 0.0025 | 0 |
| 0.02 | 100 (100) | 100 (100) | 100 (100) | 100 |
| 0.01 | 90 (72) | 70 (64) | 70 (60) | 60 |
| 0.005 | 30 (30) | 20 (10) | 0 (0) | 0 |
| 0 | 30 | 10 | 0 | |

TABLE 11

| Compound No. 1 (ppm) | Pyridaben (ppm) | | |
|---|---|---|---|
| | 200 | 100 | 0 |
| 0.02 | 100 (100) | 100 (100) | 100 |
| 0.01 | 100 (64) | 100 (60) | 60 |
| 0.005 | 30 (10) | 10 (0) | 0 |
| 0 | 10 | 0 | |

TABLE 12

| Compound No. 1 (ppm) | Pyridalyl (ppm) | | |
|---|---|---|---|
| | 1.5 | 0.4 | 0 |
| 0.02 | 100 (100) | 100 (100) | 100 |
| 0.01 | 100 (84) | 60 (20) | 20 |
| 0.005 | 100 (80) | 0 (0) | 0 |
| 0 | 80 | 0 | |

TABLE 13

| Compound No. 1 (ppm) | Spinosad (ppm) | | | |
|---|---|---|---|---|
| | 6.2 | 3.1 | 1.5 | 0 |
| 0.02 | 100 (100) | 100 (100) | 100 (100) | 100 |
| 0.01 | 80 (68) | 100 (68) | 70 (36) | 20 |
| 0 | 60 | 60 | 20 | |

TABLE 14

| Compound No. 1 (ppm) | Tebufenozide (ppm) | |
|---|---|---|
| | 1.5 | 0 |
| 0.02 | 100 (100) | 100 |
| 0.01 | 100 (52) | 40 |
| 0.005 | 20 (20) | 0 |
| 0 | 20 | |

TABLE 15

| Compound No. 1 (ppm) | Propargite (ppm) | | | |
|---|---|---|---|---|
| | 200 | 100 | 50 | 0 |
| 0.02 | 100 (90) | 100 (90) | 100 (90) | 90 |
| 0.01 | 70 (0) | 70 (0) | 57 (0) | 0 |
| 0 | 0 | 0 | 0 | |

TABLE 16

| Compound No. 1 (ppm) | Fipronil (ppm) | | |
|---|---|---|---|
| | 0.8 | 0.4 | 0 |
| 0.02 | 100 (96) | 100 (91) | 90 |
| 0.01 | 100 (60) | 100 (10) | 0 |
| 0.005 | 60 (60) | 60 (10) | 0 |
| 0 | 60 | 10 | |

TABLE 17

| Compound No. 1 | Bifenthrin (ppm) | | |
|---|---|---|---|
| (ppm) | 0.8 | 0.4 | 0 |
| 0.02 | 100 (100) | 100 (100) | 100 |
| 0.01 | 80 (46) | 20 (10) | 10 |
| 0.005 | 76 (40) | 0 (0) | 0 |
| 0 | 40 | 0 | |

TABLE 18

| Compound No. 1 | Cyromazine (ppm) | | |
|---|---|---|---|
| (ppm) | 50 | 25 | 0 |
| 0.02 | 100 (100) | 100 (100) | 100 |
| 0.01 | 100 (76) | 80 (58) | 40 |
| 0.005 | 100 (60) | 50 (30) | 0 |
| 0 | 60 | 30 | |

TABLE 19

| Compound No. 1 | Chlorfenapyr (ppm) | |
|---|---|---|
| (ppm) | 0.4 | 0 |
| 0.02 | 100 (100) | 100 |
| 0.01 | 100 (52) | 40 |
| 0.005 | 100 (20) | 0 |
| 0 | 20 | |

TABLE 20

| Compound No. 1 | Flufenoxuron (ppm) | | | |
|---|---|---|---|---|
| (ppm) | 0.04 | 0.02 | 0.01 | 0 |
| 0.02 | 100 (100) | 100 (100) | 100 (100) | 100 |
| 0.01 | 100 (68) | 100 (68) | 80 (60) | 60 |
| 0.005 | 20 (20) | 20 (20) | 0 (0) | 0 |
| 0 | 20 | 20 | 0 | |

TABLE 21

| Compound No. 1 | Azadirachtin (ppm) | |
|---|---|---|
| (ppm) | 3.1 | 0 |
| 0.02 | 100 (100) | 100 |
| 0.01 | 100 (60) | 60 |
| 0.005 | 0 (0) | 0 |
| 0 | 0 | |

TABLE 22

| Compound No. 1 (ppm) | Phenothrin (ppm) | | |
|---|---|---|---|
| | 25 | 12.5 | 0 |
| 0.02 | 100 (100) | 100 (100) | 100 |
| 0.01 | 100 (80) | 100 (20) | 0 |
| 0.005 | 100 (80) | 100 (20) | 0 |
| 0 | 80 | 20 | |

TABLE 23

| Compound No. 1 (ppm) | Acequinocyl (ppm) | | | |
|---|---|---|---|---|
| | 150 | 75 | 37.5 | 0 |
| 0.02 | 100 (100) | 100 (100) | 100 (100) | 100 |
| 0.01 | 70 (20) | 70 (20) | 30 (20) | 20 |
| 0 | 0 | 0 | 0 | |

TABLE 24

| Compound No. 1 (ppm) | Deltamethrin (ppm) | |
|---|---|---|
| | 0.4 | 0 |
| 0.02 | 100 (100) | 100 |
| 0.01 | 100 (37) | 10 |
| 0.005 | 30 (30) | 0 |
| 0 | 30 | |

TABLE 25

| Compound No. 1 (ppm) | Zeta-cypermethrin (ppm) | | | |
|---|---|---|---|---|
| | 1.5 | 0.8 | 0.4 | 0 |
| 0.02 | 100 (100) | 100 (100) | 100 (100) | 100 |
| 0.01 | 80 (28) | 56 (10) | 40 (10) | 10 |
| 0.005 | 33 (20) | 20 (0) | 0 (0) | 0 |
| 0 | 20 | 0 | 0 | |

TABLE 26

| Compound No. 1 (ppm) | Pyrifluquinazon (ppm) | | | |
|---|---|---|---|---|
| | 100 | 50 | 25 | 0 |
| 0.02 | 100 (100) | 100 (100) | 100 (100) | 100 |
| 0.01 | 60 (0) | 30 (0) | 0 (0) | 0 |
| 0 | 0 | 0 | 0 | |

TABLE 27

| Compound No. 1 (ppm) | Permethrin (ppm) | |
|---|---|---|
| | 3.1 | 0 |
| 0.02 | 100 (90) | 90 |
| 0.01 | 100 (78) | 78 |
| 0.005 | 60 (0) | 0 |
| 0 | 0 | |

TABLE 28

| Compound No. 1 (ppm) | Lufenuron (ppm) | |
|---|---|---|
| | 0.0125 | 0 |
| 0.02 | 100 (91) | 70 |
| 0.01 | 100 (82) | 40 |
| 0.005 | 100 (70) | 0 |
| 0 | 70 | |

TABLE 29

| Compound | Amitraz (ppm) | |
|---|---|---|
| No. 1 (ppm) | 62.5 | 0 |
| 0.02 | 100 (90) | 90 |
| 0.01 | 100 (78) | 78 |
| 0 | 0 | |

TABLE 30

| Compound | Fthalide (ppm) | | | |
|---|---|---|---|---|
| No. 1 (ppm) | 200 | 100 | 50 | 0 |
| 0.02 | 100 (90) | 100 (90) | 100 (90) | 90 |
| 0.01 | 100 (10) | 100 (10) | 10 (10) | 10 |
| 0 | 0 | 0 | 0 | |

TABLE 31

| Compound | Tiadinil (ppm) | | | |
|---|---|---|---|---|
| No. 1 (ppm) | 200 | 100 | 50 | 0 |
| 0.02 | 100 (70) | 90 (70) | 100 (70) | 70 |
| 0 | 0 | 0 | 0 | |

TABLE 32

| Compound | Pencycuron (ppm) | |
|---|---|---|
| No. 1 (ppm) | 125 | 0 |
| 0.02 | 100 (90) | 90 |
| 0.01 | 30 (10) | 10 |
| 0 | 0 | |

TABLE 33

| Compound | Validamycin (ppm) | | |
|---|---|---|---|
| No. 1 (ppm) | 50 | 25 | 0 |
| 0.02 | 100 (90) | 100 (90) | 90 |
| 0.01 | 30 (10) | 10 (10) | 10 |
| 0 | 0 | 0 | |

TABLE 34

| Compound | Diclocymet (ppm) | | | |
|---|---|---|---|---|
| No. 1 (ppm) | 75 | 37.5 | 18.8 | 0 |
| 0.02 | 100 (60) | 100 (60) | 60 (60) | 60 |
| 0 | 0 | 0 | 0 | |

TABLE 35

| Compound | Pyroquilon (ppm) | | | |
|---|---|---|---|---|
| No. 1 (ppm) | 200 | 100 | 50 | 0 |
| 0.02 | 80 (50) | 60 (50) | 100 (50) | 50 |
| 0.01 | 10 (0) | 0 (0) | 0 (0) | 0 |
| 0 | 0 | 0 | 0 | |

Test Example 2

Test on Controlling Effects Against Green Peach Aphid (*Myzus Persicae*)

Japanese radish leaf (cut into about 2 cm×3 cm) was put in a test tube in which water was put, and Larvae of green peach aphid were released on the leaf. On the next day, the larvae on the leaf were counted, and the leaf infested with the larvae was dipped for about 10 seconds in an insecticidal solution, dried in air and left in a constant temperature chamber at 25° C. with lightening. On the third day after the dipping, dead larvae were counted, and the mortality was calculated from the following equation. Aphids that dropped from leaf or were moribund were included in the number of dead. The evaluation results are shown in Tables 36 to 45. Further, like Test Example 1, the theoretical mortality (%) by the colby's formula are shown in brackets in Tables 36 to 45.

Mortality(%)=(number of dead insects/number of treated insects)×100

TABLE 36

| Compound | Flonicamid (ppm) | | |
|---|---|---|---|
| No. 1 (ppm) | 1.5 | 0.8 | 0 |
| 1.5 | 100 (84) | 82 (67) | 46 |
| 0.8 | 89 (72) | 80 (43) | 8 |
| 0 | 70 | 38 | |

TABLE 37

| Compound No. 1 | Azadirachtin (ppm) | | |
|---|---|---|---|
| (ppm) | 12.5 | 6.2 | 0 |
| 1.5 | 100 (94) | 100 (46) | 46 |
| 0.8 | 100 (89) | 85 (8) | 8 |
| 0 | 88 | 0 | |

TABLE 38

| Compound No. 1 | Bifenthrin (ppm) | | |
|---|---|---|---|
| (ppm) | 0.05 | 0.025 | 0 |
| 1.5 | 85 (48) | 84 (46) | 46 |
| 0.8 | 71 (11) | 79 (8) | 8 |
| 0 | 4 | 0 | |

TABLE 39

| Compound No. 1 | Imidacloprid (ppm) | | |
|---|---|---|---|
| (ppm) | 0.1 | 0.05 | 0 |
| 0.8 | 97 (69) | 83 (63) | 8 |
| 0 | 67 | 60 | |

TABLE 40

| Compound No. 1 | Probenazole (ppm) | | |
|---|---|---|---|
| (ppm) | 200 | 100 | 0 |
| 1.5 | 81 (37) | 52 (28) | 28 |
| 0.8 | 25 (23) | 29 (11) | 11 |
| 0 | 13 | 0 | |

TABLE 41

| Compound No. 1 | Flutolanil (ppm) | | |
|---|---|---|---|
| (ppm) | 250 | 125 | 0 |
| 1.5 | 60 (32) | 68 (28) | 28 |
| 0.8 | 44 (16) | 11 (11) | 11 |
| 0 | 6 | 0 | |

TABLE 42

| Compound No. 1 | Kasugamycin (ppm) | |
|---|---|---|
| (ppm) | 11.5 | 0 |
| 1.5 | 68 (28) | 28 |
| 0.8 | 11 (11) | 11 |
| 0 | 0 | |

TABLE 43

| Compound No. 1 | Tricyclazole (ppm) | | |
|---|---|---|---|
| (ppm) | 200 | 100 | 0 |
| 1.5 | 88 (28) | 55 (37) | 28 |
| 0.8 | 17 (11) | 41 (23) | 11 |
| 0 | 0 | 13 | |

TABLE 44

| Compound No. 1 | Carpropamid (ppm) | | |
|---|---|---|---|
| (ppm) | 200 | 100 | 0 |
| 1.5 | 100 (95) | 96 (87) | 28 |
| 0.8 | 95 (94) | 95 (84) | 11 |
| 0 | 93 | 82 | |

TABLE 45

| Compound No. 1 | Diclomezine (ppm) | | |
|---|---|---|---|
| (ppm) | 200 | 100 | 0 |
| 1.5 | 78 (28) | 59 (28) | 28 |
| 0.8 | 35 (11) | 11 (11) | 11 |
| 0 | 0 | 0 | |

Test Example 3

Test on Controlling Effects Against Green Rice Leafhopper (*Nephotettix Cincticeps*)

A rice seedling was dipped for about 10 seconds in an insecticidal solution and dried in air. The root was wrapped with absorbent cotton wet with water, and the rice seedling was put in a test tube. 5 Second-instar larvae of green rice leafhopper were released therein, and after covering the opening of the test tube with gauze, left in a constant temperature chamber at 25° C. with lightening (two replications were made). On the 5th or 6th day after release, dead larvae were counted, and the mortality was calculated by the following equation. Here, the insects that were moribund were counted as dead insects. The test results are shown in Tables 46 to 51.

Mortality(%)={(number of dead insects)/(number of surviving insects+number of dead insects)}×100

Further, like Test Example 1, the theoretical mortality (%) by the colby's formula are shown in brackets in Tables 46 to 51.

TABLE 46

| Compound No. 1 | Fthalide (ppm) | | | |
|---|---|---|---|---|
| (ppm) | 200 | 100 | 50 | 0 |
| 0.8 | 80 (70) | 90 (70) | 70 (70) | 70 |
| 0 | 0 | 0 | 0 | |

TABLE 47

| Compound No. 1 | Mepronil (ppm) | |
|---|---|---|
| (ppm) | 187.5 | 0 |
| 0.8 | 100 (90) | 90 |
| 0.4 | 50 (30) | 30 |
| 0.2 | 10 (0) | 0 |
| 0 | 0 | |

TABLE 48

| Compound No. 1 | Azoxystrobin (ppm) | |
|---|---|---|
| (ppm) | 25 | 0 |
| 0.8 | 100 (93) | 90 |
| 0.4 | 80 (65) | 50 |
| 0 | 30 | |

TABLE 49

| Compound No. 1 | Isoprothiolane (ppm) | |
|---|---|---|
| (ppm) | 200 | 0 |
| 0.8 | 100 (85) | 70 |
| 0.4 | 100 (80) | 60 |
| 0.2 | 90 (60) | 20 |
| 0 | 50 | |

TABLE 50

| Compound No. 1 | Diclocymet (ppm) | | |
|---|---|---|---|
| (ppm) | 0.8 | 0.4 | 0 |
| 0.8 | 100 (100) | 100 (100) | 100 |
| 0.4 | 100 (90) | 100 (90) | 90 |
| 0 | 0 | 0 | |

TABLE 51

| Compound No. 1 | Probenazole (ppm) | |
|---|---|---|
| (ppm) | 200 | 0 |
| 0.8 | 60 (40) | 40 |
| 0.4 | 27 (10) | 10 |
| 0 | 0 | |

Test Example 4

Test on Controlling Effects Against Housefly (*Musca Domestica*)

10 g of a culture medium is put into a plastic cup having a diameter of 6 cm and a height of 3 cm, and then, 10 ml of an insecticidal solution prepared to bring the predetermined concentration of the compound of the present invention is added and mixed. 20 to 30 hatched larvae are released, and after putting a cover thereon, the cup is left in a constant temperature chamber at 25° C. with lightening for about 2 weeks. Thereafter, the number of adults is counted, and the percent inhibition of emergence is obtained by the following equation.

Percent inhibition of emergence(%)=(1−(number of adults/number of released larvae))×100

Further, the theoretical percentage inhibition of emergence (%) can be calculated by the colby's formula. The pesticidal composition of the present invention provides a percent inhibition of emergence (%) higher than the theoretical value (%) and thereby has a synergistic effect regarding controlling of pests.

Test Example 5

Test on Controlling Effects Against Formosan Subterranean Termite (*Coptotermes formosanus*)

A filter paper is laid in a glass petri dish having a diameter of 9 cm, and 1 ml of an insecticidal solution prepared to bring the predetermined concentration of the compound of the present invention is applied. Then, 10 workers and one soldier of Formosan subterranean termite are released, and after putting a cover, the petri dish is left in a constant temperature chamber at 25° C. with lightening. After about one week from the treatment, the number of dead workers is counted, and the mortality is obtained by the following equation.

Mortality(%)=(number of dead workers/10)×100

Further, like Test Example 1, the theoretical mortality (%) can be calculated by the colby's formula. The pesticidal composition of the present invention provides a mortality (%) higher than the theoretical mortality (%) and is thereby has a synergistic effect regarding controlling of pests.

Test Example 6

Test on Controlling Effects Against *Haemaphysalis Longicornis*

On an inner surface of a petri dish having a diameter of 9 cm, 1 ml of an acetone solution prepared to bring the predetermined concentration of the compound of the present invention is dropwise applied by a micropipette. After the inner surface of the petri dish is dried, about 100 larval ticks are put, and the petri dish is covered with a polyethylene sheet and sealed. The number of knockdown ticks after the contact with the solution is recorded, and the knockdown rate is obtained by the following equation.

Knockdown rate(%)=(number of knockdown ticks/number of released larvae)×100

Further, the theoretical knockdown rate (%) can be calculated from the colby's formula. The pesticidal composition of the present invention provides a knockdown rate (%) higher than the theoretical knockdown rate (%) and thereby has a synergistic effect regarding controlling of pests.

Test Example 7

Test on Controlling Effects Against Cat Flea (*Ctenocephalides Felis*)

0.5 ml of an acetone solution prepared to bring the predetermined concentration of the compound of the present invention is dropped in a glass tube having a flat bottom (inner diameter: 2.6 cm, bottom area: 5.3 $cm^2$, height 12 cm). Acetone is evaporated at room temperature to form a dry film containing the compound of the present invention on the bottom surface. Ten adults of cat flea (not-yet-blood-sucked adults within five days after adult emergence) are put. The number of dead fleas after the contact with the dry film is recorded, and the mortality (%) is obtained by the following equation.

Mortality(%)=(number of dead insects/number of released insects)×100

Further, like Test Example 1, the theoretical mortality (%) can be calculated by the Colby's formula. The pesticidal composition of the present invention provides a mortality (%) higher than the theoretical mortality (%) and thereby has a synergistic effect regarding controlling of pests.

The entire disclosures of Japanese Patent Application No. 2006-336585 filed on Dec. 14, 2006 and Japanese Patent Application No. 2007-105029 filed on Apr. 12, 2007 including specifications, claims and summaries are incorporated herein by reference in their entireties.

The invention claimed is:

1. A method for controlling pests which creates problems in agricultural and horticultural fields, by applying synergistically effective amounts of N-[2-bromo-4-chloro-6-[[α-methyl-(cyclopropylmethy)amino]carbonyl]-phenyl]-3-bromo-1-(3-chloro-2-pyridyl)-1H-pyrazole-5-carboxamide or a salt thereof; and an insecticide to the pests or plants,
wherein the insecticide is flonicamid;
and wherein the weight ratio of N-[2-bromo-4-chloro-6-[[α-methyl-cyclopropylmethy)amino]carbonyl]-phenyl]-3-bromo-1-(3-chloro-2-pyridyl)-1H-pyrazole-5-carboxamide or a salt thereof to the insecticide is from 1:10000 to 2:1.

* * * * *